(12) United States Patent
Vasudeva et al.

(10) Patent No.: US 8,904,701 B2
(45) Date of Patent: Dec. 9, 2014

(54) BED BUG TRAP

(76) Inventors: Kailash C. Vasudeva, Waterloo (CA); Satnam Singh, Kitchener (CA)

( * ) Notice: Subject to any disclaimer, the term of this patent is extended or adjusted under 35 U.S.C. 154(b) by 383 days.

(21) Appl. No.: 13/437,032

(22) Filed: Apr. 2, 2012

(65) Prior Publication Data

US 2012/0246998 A1 Oct. 4, 2012

Related U.S. Application Data

(60) Provisional application No. 61/470,229, filed on Mar. 31, 2011, provisional application No. 61/483,830, filed on May 9, 2011.

(51) Int. Cl.
*A01M 1/10* (2006.01)
*A01M 1/02* (2006.01)
*A01M 1/14* (2006.01)

(52) U.S. Cl.
CPC ............... *A01M 1/023* (2013.01); *A01M 1/103* (2013.01); *A01M 1/14* (2013.01)
USPC ............................................. 43/123; 424/84

(58) Field of Classification Search
USPC ............................................. 43/123; 424/84
See application file for complete search history.

(56) References Cited

U.S. PATENT DOCUMENTS

| | | | |
|---|---|---|---|
| 668,775 A | 2/1901 | Herfert | |
| 1,970,774 A | 8/1934 | Shinner | |
| 2,356,022 A | 8/1944 | Wright | |
| 5,327,675 A * | 7/1994 | Butler et al. | 43/113 |
| 8,211,419 B2 * | 7/2012 | Siljander et al. | 424/84 |
| 8,316,578 B2 * | 11/2012 | Faham et al. | 43/123 |
| 8,402,690 B2 * | 3/2013 | Schneidmiller et al. | 43/123 |
| 8,707,615 B2 * | 4/2014 | Cullen | 43/123 |
| 2009/0145019 A1 * | 6/2009 | Nolen et al. | 43/121 |
| 2009/0145020 A1 | 6/2009 | McKnight | |
| 2009/0260276 A1 * | 10/2009 | Kirsch et al. | 43/114 |
| 2009/0282728 A1 | 11/2009 | McKnight et al. | |
| 2011/0203159 A1 | 8/2011 | McKnight | |
| 2013/0180162 A1 * | 7/2013 | Vasudeva et al. | 43/123 |
| 2014/0090290 A1 * | 4/2014 | Baschnagel, III | 43/123 |

FOREIGN PATENT DOCUMENTS

CA 2511015 A 12/2005

* cited by examiner

*Primary Examiner* — Christopher P Ellis

(57) ABSTRACT

A bed bug trap includes heat, carbon dioxide and/or semiochemicals (pheromones and/or kairomones), to attract and trap bed bugs. The trap may be combined with the appearance and/or function of another appliance, such as an air freshener. The release of semiochemicals may be combined with the release of air freshening compositions. The bed bug trap may provide one attraction mode, or two attraction modes, namely one which uses heat, carbon dioxide and/or kairomones to attract bed bugs seeking a meal, and the other which uses pheromones to attract bed bugs seeking a safe harbor, i.e. a hiding place. The bed bug trap may be combined with a wide variety of appliances, such as air fresheners, alarm clocks, clock radios, humidifiers, desk or table lamps, power bars, etc.

12 Claims, 12 Drawing Sheets

BED BUG TRAP

REFERENCE TO RELATED APPLICATION(S)

This application is a formal application based on and claiming the benefit of provisional application Ser. No. 61/470,229, filed Mar. 31, 2011, and provisional application Ser. No. 61/483,830, filed May 9, 2011.

BACKGROUND OF THE INVENTION

This invention relates to bed bug traps, especially but not necessarily in combination with other appliances. In particular, the invention provides a bed bug trap with a combination of bed bug attractants, and which may include the function and appearance of a complementary appliance, such as an air freshener, clock, radio, lamp or the like.

Bed bug traps of various types have been gaining increasing prominence and attracting increased market attention as the bed bug problem, well known outside North America, becomes more pronounced in North America.

A significant problem associated with bed bug traps is that their presence may be an undesirable indication to a guest that there is a bed bug risk, whether that is in someone's home, or in a commercial setting such as an office, or especially in a hotel room, and especially in the developed world where there is a good deal of paranoia around bed bug issues. This problem will often deter the owner from deploying a trap, despite how the trap might be otherwise highly desirable, since the owner wants to avoid the stigma often associated with having bed bugs. This fear of stigma certainly deters the owner from deploying a trap prophylactically, as a means of detecting an imminent problem. Preferably, any property owner who suspects a bed bug infestation or who wants to guard against one should not be deterred from deploying a trap prophylactically, so that an incipient problem can be dealt with before it develops into a major infestation.

With any bed bug trap, it is of course desirable to attract bed bugs to the trap. There are various known ways of doing this. For example, it is well known that carbon dioxide and warmth act as bed bug attractants, particularly when the bed bugs are seeking to feed. A number of luring compositions are also known, including various semiochemicals (pheromones and kairomones). It is known that certain pheromones will attract bed bugs seeking a safe place to harbor, and that certain kairomones will attract bed bugs seeking a feeding location, such as a human host.

Throughout this specification, whenever the terms "semiochemical" or "pheromone" or "kairomone" are used, it should be understood that this is intended to mean only such of those substances as are known to be attractants for bed bugs, or as may become known to be attractants for bed bugs or believed to be attractants for bed bugs.

Once the bed bugs have be lured to the trap, it is of course important to actually trap them so that they do not escape. Various means have also been employed to actually trap the bed bugs. These include, for example, various pitfall configurations and glue strips or the like.

In view of the preceding, it would therefore be advantageous to combine the bed bug trap with another common appliance, not only to avoid the appearance of a bed bug trap, but also to provide the increased functionality of that appliance.

BRIEF SUMMARY OF THE INVENTION

It is therefore an object of the invention to provide a device which is effective as a bed bug trap, but which preferably but not necessarily also provides the appearance and/or function of another appliance, or of some device of unknown function.

When the trap is combined with an air freshener, for example, the visitor or hotel room guest would just perceive the device as an air freshener, not knowing that it also serves as a bed bug trap.

The device preferably is powered, but not necessarily. In the case of the bed bug trap being combined with a functioning air freshener, for example, the air freshening feature may not require power, and some bed bug traps do not require power.

The bed bug trap may include means for generating heat, carbon dioxide and/or kairomones and/or pheromones, as will be explained in greater detail later herein.

The bed bug trap may provide two attraction modes, one of which uses heat, carbon dioxide and/or kairomones to attract bed bugs seeking a meal, and the other of which uses pheromones to attract bed bugs seeking a safe harbor, i.e. a hiding place. The bed bug trap may have these two different modes operating simultaneously in different areas, or may be switchable between modes, for example via a timer, or in response to some trigger such as a light sensor. Alternatively, one mode may operate continuously, for example the mode in which bed bugs are attracted to a harboring location, while the other mode, for example the mode in which bed bugs are attracted to a feeding location, may be operated only intermittently. Or of course the bed bug trap may be designed to operate in just one of these modes, i.e either mimicking a harboring location or a feeding location, but not both.

The bed bug trap may be given the appearance of, or be combined with, a wide variety of appliances, such as air fresheners, clock radios, humidifiers, desk or table lamps, power bars, etc. This list should not be considered exhaustive. In each case, the device should have the general appearance of the appliance, with the bed bug trap either completely hidden, or at least not readily discernible.

Thus if a person sees the device in someone's home or office or in a hotel room, for example, he or she is not alerted to a possible bed bug concern. It is a further advantage of the device that it may be used preventatively or prophylactically, whether or not there is a known bed bug infestation. Thus a hotel may have such a device in every room, simply to guard against the development of an infestation, or to warn staff when there might be a developing problem. If maintenance or cleaning staff find a bed bug or bed bugs in the trap, they will know that more aggressive measures may be needed.

In addition to the advantage of disguising the bed bug trap function, the device may offer the advantage of combining two or more functions in one device, so that the home owner or hotel operator does not need to purchase separate devices. Furthermore, in powered devices the power supply used for the apparent function can be shared with the power needs of the hidden function, i.e. the bed bug trap. Other features may be shared as well. For example, in the case of an air freshener, the same means for releasing kairomones and/or pheromones potentially may be used to release air freshening compositions.

Further details of the invention will be described or will become apparent in the course of the following detailed description and drawings of specific embodiments of the invention, as examples.

BRIEF DESCRIPTION OF THE DRAWINGS

Embodiments of the invention will now be described, by way of example only, with reference to the attached drawings, in which.

DETAILED DESCRIPTION OF THE INVENTION

Basic Examples of the Invention

Figure 1:
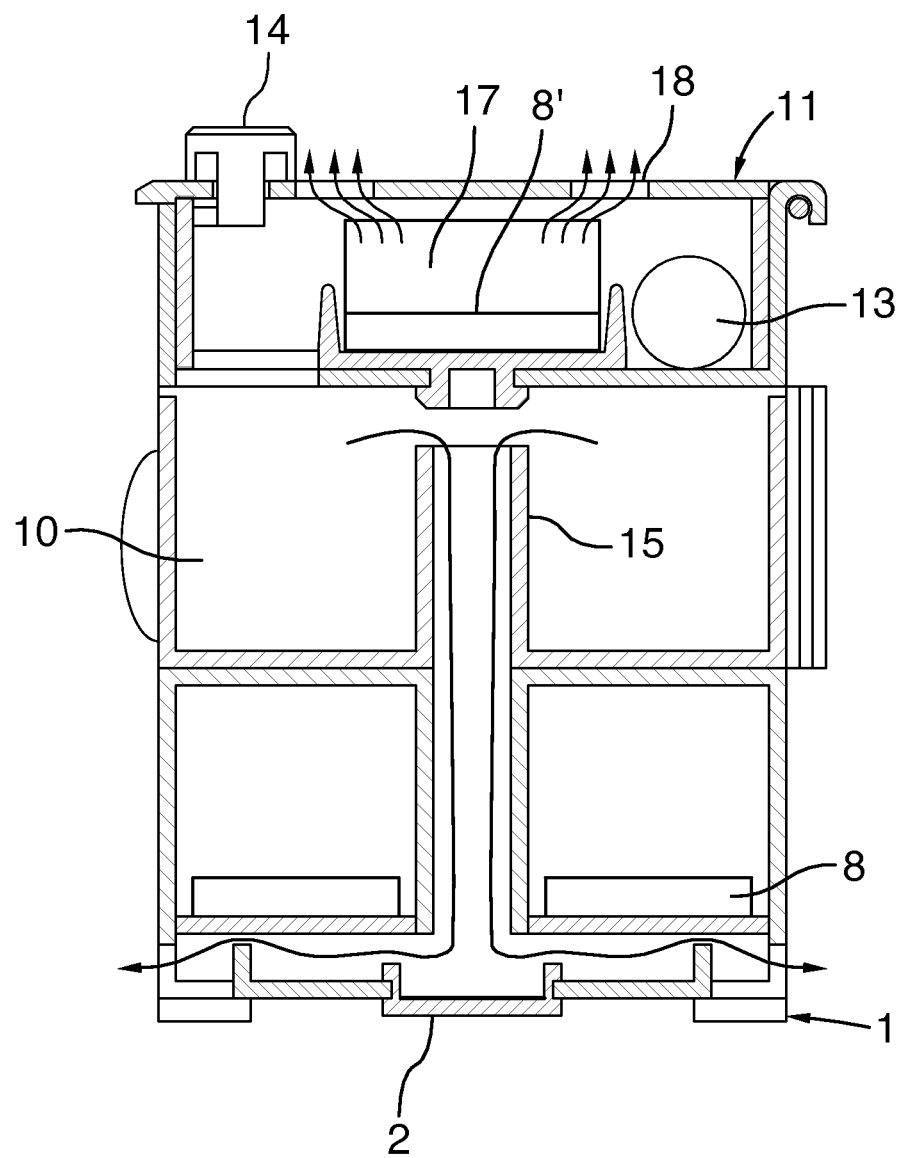
FIG. 1 is a cross-sectional schematic view of an early conceptual design of one example of the invention, combining a bed bug trap with an air freshener.
Figure 2:
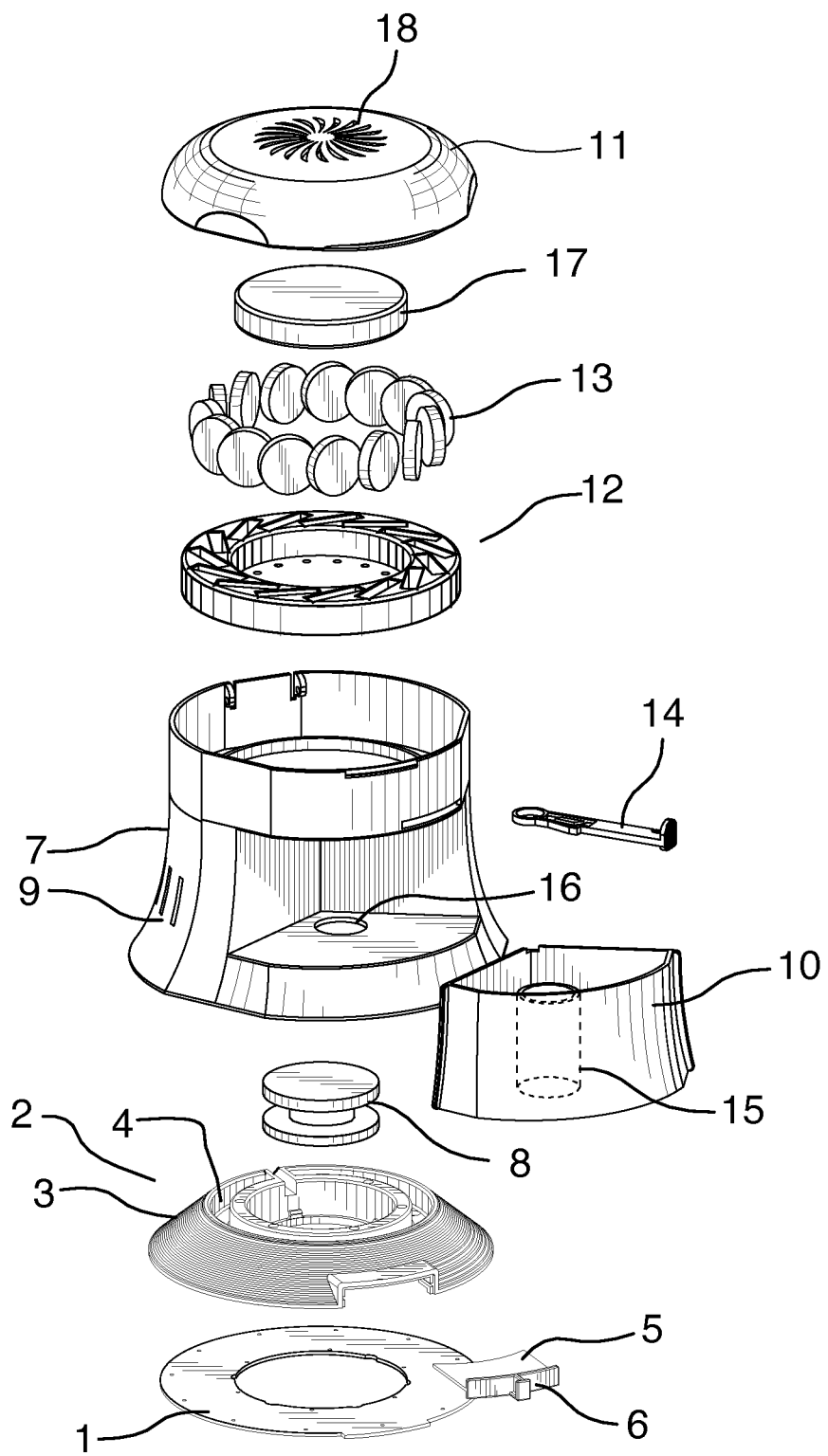
FIG. 2 is an exploded perspective view of a later example of the invention, again combining a bed bug trap with an air freshener.
Figure 3:
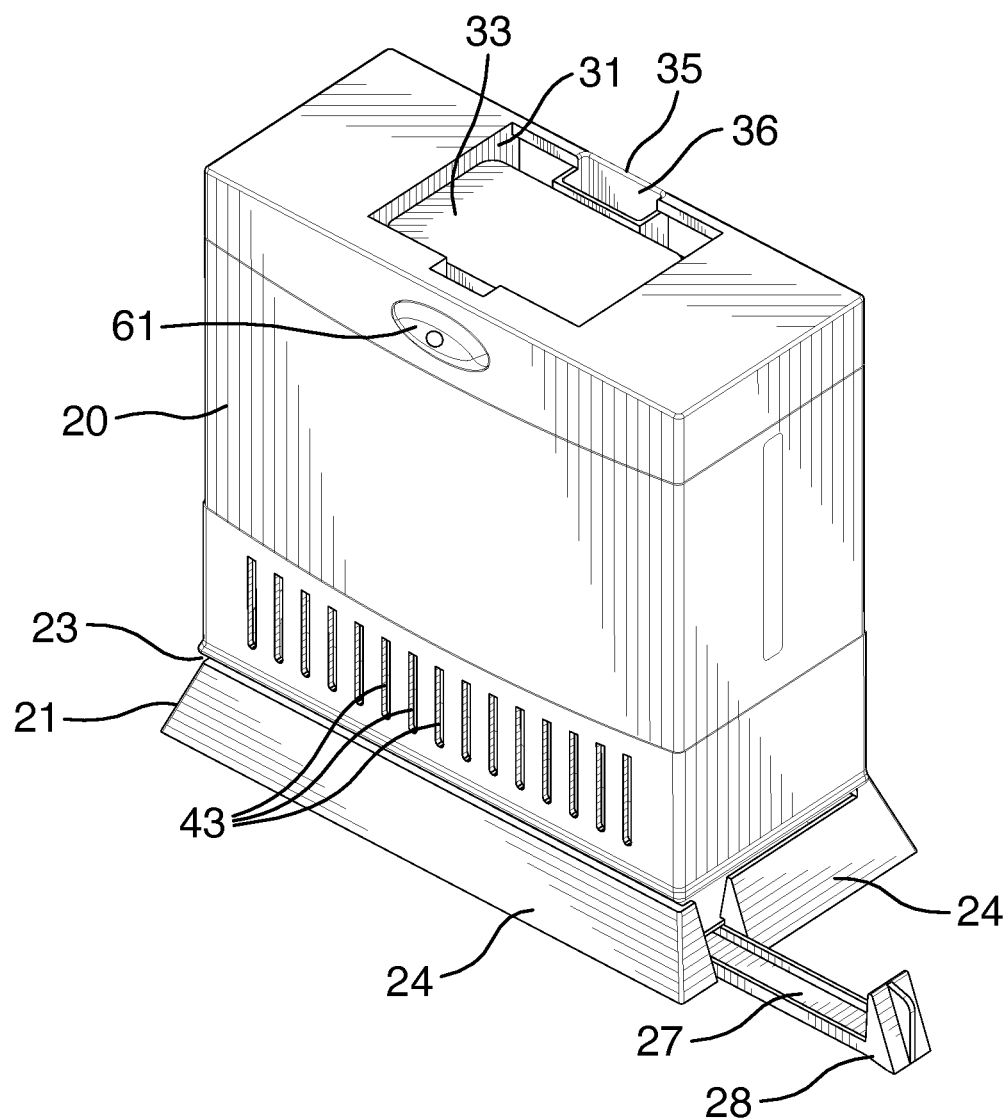
FIG. 3 is a front perspective view of a dual-mode bed bug trap and air freshener.

First and second examples of the invention are illustrated in FIGS. 1 and 2. In these examples, a bed bug trap is combined with an air freshener. As discussed above, the bed bug trap could simply be given the appearance of an air freshener, or some other common structure or appliance, but in these examples a functioning air freshener is provided.

FIG. 1 is an early conceptual design, shown here to illustrate the principle. FIG. 2 is a later embodiment. It should be noted that these embodiments are somewhat different from each other, having been produced at different times as the design has evolved. For example, FIG. 1 shows a removable bottom plug as the bed bug trap, instead of the replaceable drawer of FIG. 2, and there are a number of other differences which will become apparent. Except where otherwise noted, the following description relates to FIG. 2. However, both drawings illustrate the same inventive principle.

The device has a base plate 1 on which is mounted a bed bug trapping element 2, which may comprise, for example, a textured surface 3 which a bed bug can climb, leading to a pitfall 4. Although not very visible in FIG. 2, the pitfall is essential an annular channel at an upper edge of the textured surface 3, having generally vertical smooth side walls, such that once the bed bug falls in, it is unable to get out. The channel has one or more holes in the bottom thereof, for bed bugs to exit, whereupon they fall onto or are routed to a trapping glue surface 5 on a removable and replaceable drawer 6. The glue may be any suitable glue which is sufficient to capture bed bugs such that they cannot escape. Pitfall traps for bed bugs are known in the prior art, and any configuration of such a trap could be used, as could traps of other types, including glue traps.

A main housing 7 is mounted over the base plate 1 and trapping element 2, extending down to near the surface on which the device rests, but leaving a small enough gap for bed bugs to enter.

It is well known that bed bugs are attracted to warmth and to carbon dioxide. Thus within the main housing 7, in a central recess of the trapping element 2, is a small heating element 8 designed to produce a temperature preferably in the range of 37 to 39 degrees Celsius, to approximately mimic body heat. The housing has vent holes 9 for the warmth to escape.

In a portion of the main housing 7 is a water chamber 10. The water chamber may contain water, or preferably a number of "water beads" or the like, which are highly absorbent beads which fill with water and swell from about the size of a grain of rice up to about ½ inch or 1-1.5 cm in diameter. Commonly used for growing house plants, they retain a "wet" feel, and gradually give up their water.

The main housing has a readily removeable lid 11, under which is a carousel assembly 12. The carousel assembly has a number of vertically-oriented slots, each to hold one of a number of carbon dioxide generating tablets 13, which generate carbon dioxide when in contact with water. One suitable brand is "$CO_2$ Fizz Tabs" sold by "Jungle Plant Care Solutions", for example. The carousel assembly includes a ratchet mechanism (not shown) operated by a spring-loaded lever 14 to index the mechanism one slot at a time, to align a tablet with a fixed-location slot such that it falls through that slot into the water chamber 70. The aforementioned water beads are preferable to water, since they produce a slower release of carbon dioxide.

The carbon dioxide escapes down a tube 15 in the water chamber and out through the hole 16 to the area of the trapping element 2. This encourages bed bugs to enter the device through the small gap at the bottom of the main housing 7. Each carbon dioxide tablet may last for 3 or 4 hours, and in the preferred embodiment there are spaces for fifteen tablets. The tablets may be easily replaced by flipping off the top of the upper housing, and reloading the carousel. Since the device is not likely to be used continuously, it is anticipated that in normal usage the carousel will need to be recharged with tablets perhaps only every 3 or 4 weeks or more.

Other means of carbon dioxide production of course could be used. For example, carbon dioxide could be released slowly or in a programmed intermittent fashion, from a carbon dioxide cylinder. Other means will be described later herein.

In the center of the upper part of the device, i.e. under the lid 11, is a fragrance puck 17, which may be a conventional fragrance puck, or which may be combined with a semiochemical to release the semiochemical along with the fragrance. The fragrance, and semiochemical if applicable, is slowly released by the puck, as with conventional air fresheners, through vent holes 18 on the top of the device. Preferably the lid 11 is secured to the main housing 7 in such a way that there is a small gap between the two, to facilitate air flow. To enhance the release of the fragrance and/or semiochemical, an optional heating element 8' may be provided underneath or in the vicinity of the fragrance puck.

The device is provided with an on/off switch (not shown) for the heating element 8, and for the optional heating element 8' if applicable.

If desired, the device could be rendered automatic in several ways. For example, the heating element could be on a timer, to shut off after a certain amount of time. Or it could be programmable, to operate only at certain intervals or certain times of day, or in response to certain room conditions, such as whether or not the room is dark, as determined by a light sensor incorporated into the device.

Similarly, the carousel could be controlled to automatically rotate to the next position only at some fixed or programmable time interval. A warning light could be provided, either to show that there are no remaining carbon dioxide tablets, or that there are only a certain number remaining.

Preferably, the device is powered. Most simply, this may be by a plug-in electrical cord, or by a plug protruding from the back of the device if configured for wall mounting at an electrical outlet. Alternatively, the power may be supplied from a battery pack, using either disposable batteries, or preferably rechargeable batteries.

In a powered version, the power may be employed to power a small heating element, whether constantly or intermittently, to aid in attracting bed bugs. The power may also be used by timing elements, where intermittent operation is desired, or in the case of a dual-mode device, to switch between modes (for example, by opening and closing appropriate shutters, or rotating or lifting movable parts).

Dual Mode Devices

It is known that bed bugs, when not seeking to feed, will seek out safe hiding places or harbors, in what may be referred to as harboring behavior. They are attracted to such harbors by pheromones emitted by other bed bugs. Heat and carbon dioxide may actually deter the bed bugs who are seeking safe harbor. Therefore, in one mode of operation, the bed bug trap will release pheromones, without heat and/or carbon dioxide.

It is also known that bed bugs, when hungry and seeking to feed, will be attracted by heat, carbon dioxide and kairomones. Therefore, in a second mode of operation, the bed bug trap will provide one, two or preferably all three of these attractants, i.e. heat, carbon dioxide and kairomones.

The bed bug trap may be designed to operate in only one of these two modes, or may be designed as a dual-mode device. The dual modes may operate simultaneously, in different areas of the device, or a mechanism may be provided to switch from one mode to the other. Such mechanisms may include, for example, in addition to turning heat and carbon dioxide generation on and off: shutters which open and close as desired, to switch between kairomones and pheromones; a rotatable collar where rotation selectively opens and closes certain ports for kairomone or pheromone release; a movable body portion; or other like means.

In a two-mode device, various means can be employed to determine when to switch between modes, if the design is such that the two modes are not in simultaneous operation. Since bed bugs seek harbor more often than they seek food, it is reasonable to set the device for "harbor" mode most of the time, i.e. with no heat or carbon dioxide, and with release of pheromones, not kairomones. However, when a person is present, it may be preferable to switch to "feeding" mode, i.e. with heat, carbon dioxide generation and kairomones instead of pheromones, so that any bed bugs wanting to feed hopefully will head for the bed bug trap instead of for the person.

Switching between modes can be done on a time basis. Where the device is integrated with a clock or clock radio, for example, this is easily accomplished using the clock of the device. The trap can be switched to feeding mode at a set time every day, for example in the evening and night when a person is more likely to be present, and can be set to harbor mode during the day.

Similarly, a light sensor can be provided, such that the device is in harbor mode when there is light, but switches to feeding mode when the light is off.

In many hotels, especially in Europe for example, power is provided to the hotel room only when the occupant places his or her key or key card in a slot near the door. The device could switch to feed mode only when the room is powered, by plugging into an outlet which is powered only when the room is powered, with automatic switching back to harboring mode when the power is off. For example, a solenoid could maintain the device in feeding mode as long as there is power, but removing power could cause the device to spring back to harboring mode.

In some hotels or "smart houses", especially as technology progresses, the devices might be remotely controlled, for example from the hotel front desk, so that the mode could be switched remotely, either on demand, or in accordance with some programmed schedule.

Dual Mode Air Freshener

FIGS. 3-7 illustrate another example of a bed bug trap combined with an air freshener. In this example, an upper body 20 is supported above a base 21 by pedestals 22. The upper body is separated from the base around the front and sides by a small gap 23. Bed bugs seeking to feed are attracted to climb the textured ramp portions 24 around the front and sides of the base and thence through the gap 23, where they then encounter a pitfall, falling onto a surface 25 of the base. The surface 25 has one or more holes 26 through it, to which the bed bugs will migrate. When they fall through the holes, they fall onto a glue strip 27 mounted on the upper surface of a drawer 28. Either the drawer itself is removable and replaceable as a complete assembly, or just the glue strip is removable and replaceable, so that the presence of any bed bugs can be detected, and they can be removed.

To attract bed bugs to this portion of the trap, preferably heat, carbon dioxide and kairomones are provided, though it should be appreciated that in some embodiments only one or two attraction means might be employed. For example, in an unpowered version of the device, only carbon dioxide and a semiochemical, e.g. a kairomone, might be provided, to attract bed bugs seeking a feeding location. As another example, only a semiochemical might be provided, such as a kairomone to attract bed bugs seeking a feeding location, or a pheromone to attract bed bugs seeking a hiding or "harboring" location.

However, in the preferred version of this embodiment, heat, carbon dioxide and kairomones are supplied to this portion of the device, to attract bed bugs seeking a feeding location, and additionally pheromones are supplied at a different portion of the device to attract bed bugs seeking a harboring location. Air freshening compositions may be released at either or both locations. The device is thus a dual-mode device, i.e. attracting both bed bugs wishing to feed, and bed bugs seeking to harbor.

The trap for bed bugs seeking a harboring location will now be described, before turning to a description of the carbon dioxide and heat generating means for the bottom portion of the device.

Figure 4:
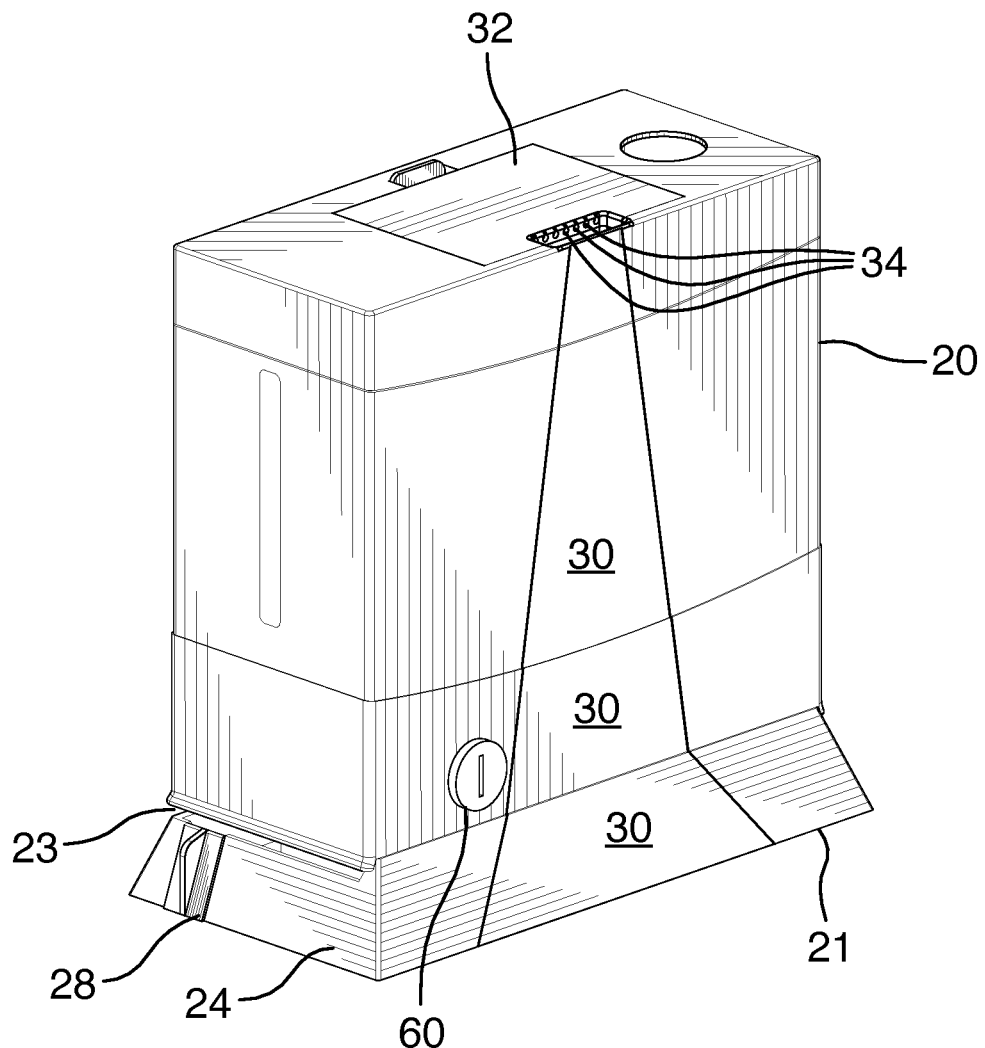
FIG. 4 is a perspective view of the back of the FIG. 3 device.

FIG. 4 shows the back of the device. Note that the gap 23 does not extend around the back of the device. Instead, there is an essentially continuous back surface, which is sufficiently smooth that bed bugs cannot climb it, except for a central portion 30. The central portion 30 is sufficiently textured that bed bugs can climb it, the intent being that they will do so to seek a harboring location. At the top of the device is a compartment 31 with a cover 32 (the cover being shown in FIG. 4 only). In the compartment is a removable and replaceable block or puck 33 which slowly gives off pheromones, though small holes 34 to attract the bed bugs seeking to harbor. Preferably, the composition of the puck 33 is such that it emits not only pheromones, but also an air freshening composition.

Bed bugs climbing the central portion 30 in response to the pheromones reach a precipice 35, from which they fall down a chute 36 to the base of the device, onto the previously mentioned surface 25. From there, they migrate to the holes 26 and are captured on the glue strip 27. If desired, partition walls 28 may be used to block bed bugs which fall from the "harboring" trap from mingling with bed bugs attracted to the "feeding" trap, so that when the glue strip is replaced, it can be determined from which trapping area the bed bugs arrived. However, in most cases that information is not useful, so this feature is purely optional.

Instead of a chute 36 leading down to a shared pitfall trap as just described, of course the harboring trap could be provided with its own separate pitfall trap, for example at the upper location, complete with a separate removable drawer and glue strip.

Figure 5:
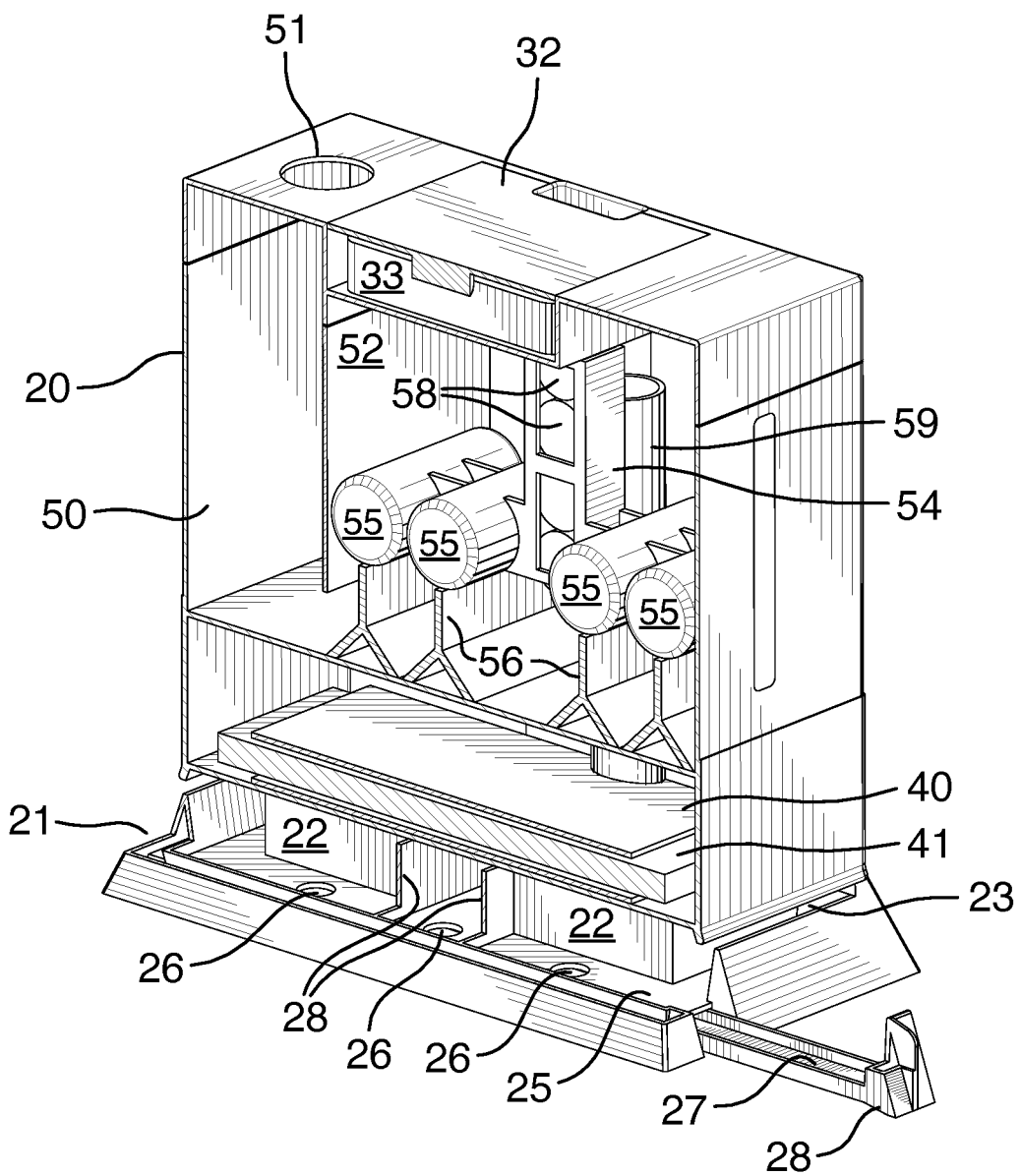
FIG. 5 is front perspective view corresponding to FIG. 3, but cut open to show the internal structure and features.
Figure 6:
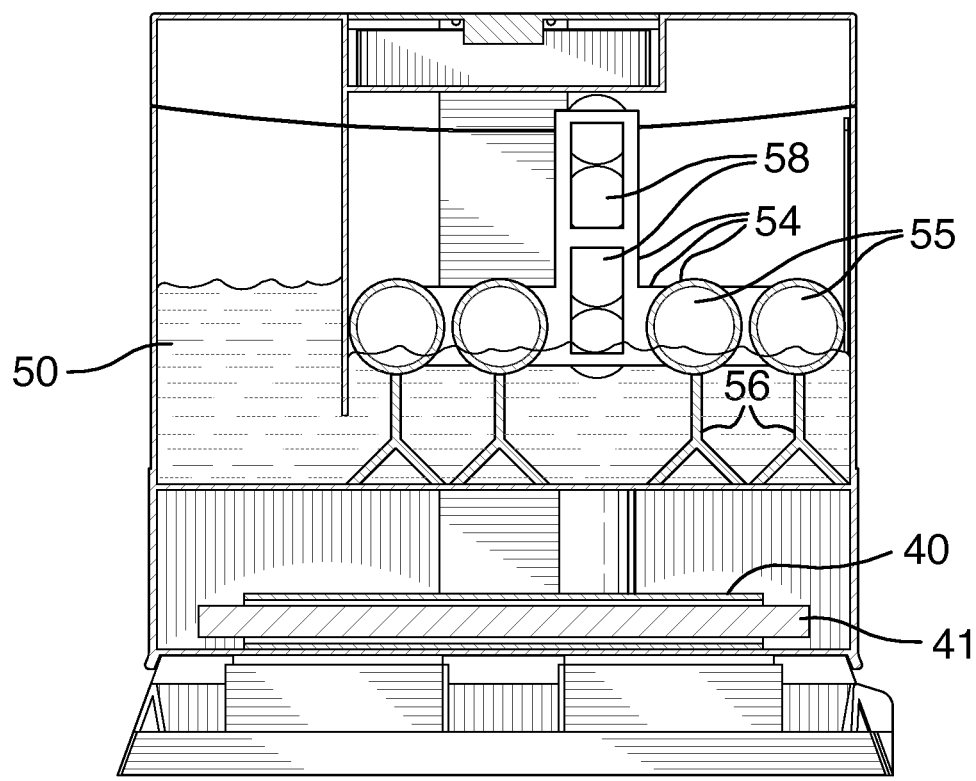
FIG. 6 is a front cutaway view of the interior of the FIG. 3 device, showing carbon dioxide generating tablets in contact with water to generate carbon dioxide.
Figure 7:
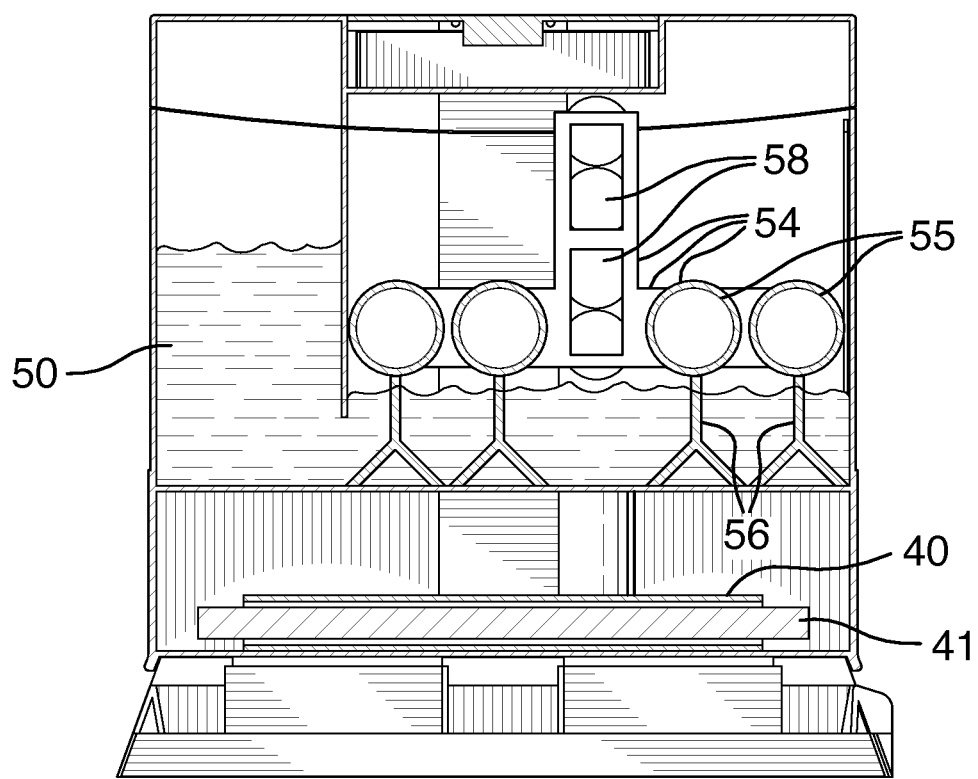
FIG. 7 is a front cutaway view similar to FIG. 6, with the water level forced below the level of the carbon dioxide generating tablets.

Referring now to FIGS. 5-7, the carbon dioxide and heat generation means for the lower portion of the device will now be described. Of course it should be understood that any suitable means of generating heat and/or carbon dioxide could be employed, the following being just one example. For example, in an unpowered device, a replaceable heat pack could be employed.

Preferably, however, the device is powered, whether by plugging into an electrical outlet (preferably), or battery-operated. A heating element 40 warms a block or puck 41 in a lower portion of the upper body 20. The puck 41 releases kairomones, and preferably also an air freshening composition, whether or not the air freshening composition is also provided at the harboring trap location. When provided at both locations, air freshening will occur even if the puck at one location is fully expended. The kairomones and optional air freshening composition escapes via slots 43 in the front of the device, and/or into the pitfall trap via small holes beneath the puck location (not shown).

Above the compartment with the heating element 40 and puck 41 is a water tank 50, fillable from an opening 51. The tank is partially divided into two sections, namely a fill portion and a float portion, by a partition 52 which extends down from the roof of the water tank but not all the way to the bottom of the tank.

In the float portion is a float assembly 54, with several floats 55. The float assembly floats up and down on a central post (not visible in the drawings), but is prevented from dropping to the bottom of the tank by float stops 56.

The center portion of the float assembly includes a refillable slot which carries tablets 58 which generate carbon dioxide on contact with water. The carbon dioxide so generated falls down the tube 59 and into the pitfall trap area to attract bed bugs thereto. So that the flow of carbon dioxide may be shut off, the tube includes a carbon dioxide release valve (not specifically shown), which may be operated for example via a manual control 60 on the back of the device, or by automatic means such as a timer or light sensor 61.

FIGS. 6 and 7 show the operation of the carbon dioxide generation. In FIG. 6, the float assembly 54 has not dropped far enough to contact the float stops 56. The lowermost tablet 58 is therefore in contact with water, and generates carbon dioxide, which rises in the float portion of the tank, and either falls down the tube 59 at a rate set by the carbon dioxide release valve, or fills the chamber if the valve is closed. In either event, as soon as there is more carbon dioxide being produced than is being dispensed, the water level in the float portion is displaced downwardly until the floats 55 contact the stops 56 and the tablet is no longer in contact with water. The production of carbon dioxide is thus self-limiting, such that no more carbon dioxide is produced than is needed.

Alarm Clock, Radio or the Like

Figure 8:
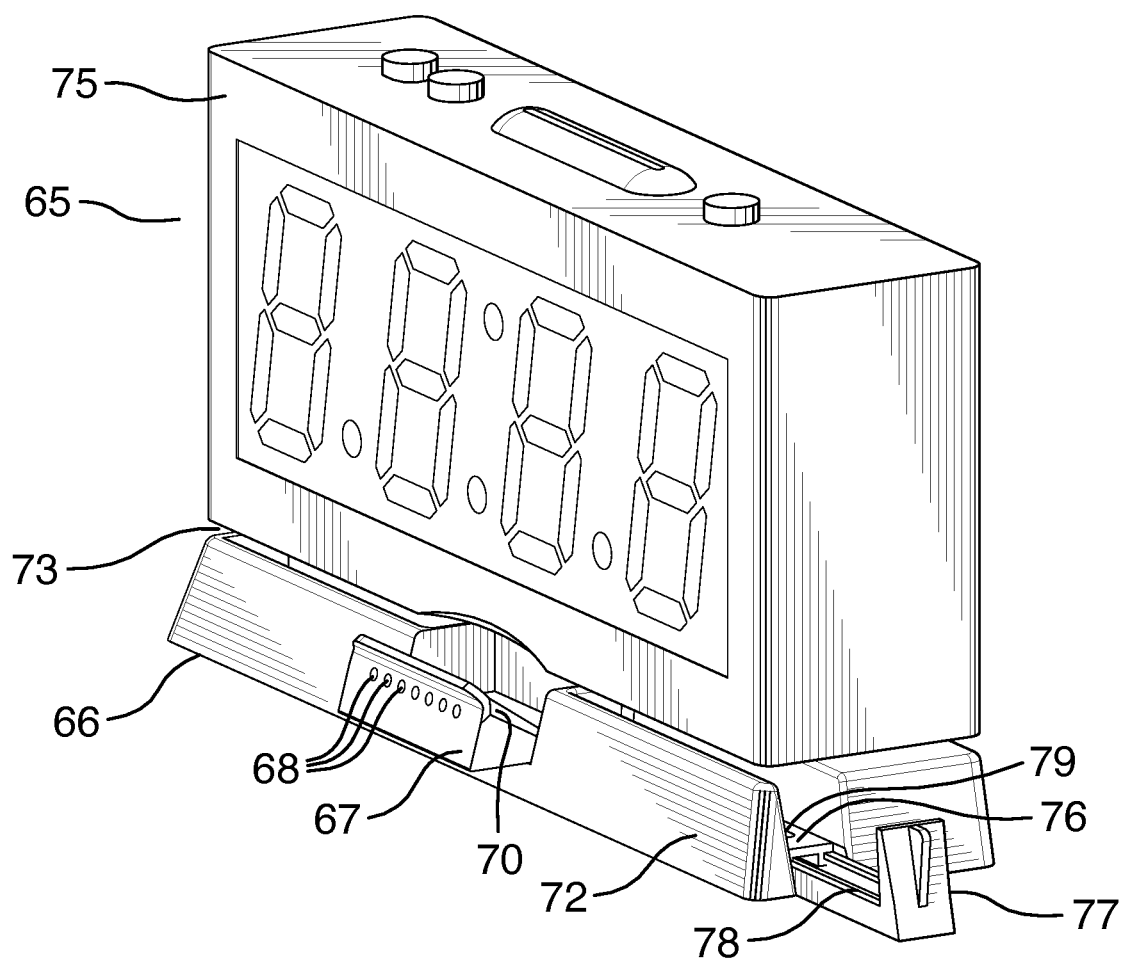
FIG. 8 is a perspective view of an alarm clock or clock radio or the like, incorporating a bed bug trap.

FIG. 8 shows an example of an alarm clock 65, clock radio, radio or the like according to the invention. The body of the device has a base portion 66 with a slide-out drawer 67, the drawer having a front face with a number of small holes 68. The interior of the drawer includes a platform on which a semiochemical-releasing medium 70, such as a pheromone impregnated pad, is mounted. The pheromone escapes slowly through the small holes, to attract bed bugs who are seeking a harboring location. The bed bugs enter the body by climbing the ramped portion 72 of the base, which has sufficient texture for them to be able to climb, and then passing through a small gap 73 between the base portion 66 and the upper body 75 of the device. (The front of the drawer 67 is made sufficiently smooth that bed bugs cannot climb it.) The bed bugs then encounter a pitfall, falling onto the surface 76. A second slide-out drawer 77 under the surface 76 has an elongated platform which carries a glue strip 78 or the like. The surface 76 has one or several holes 79 in it, through which the bed bugs fall and are captured by the glue strip. Both drawers are removable and replaceable, so that the pheromone release may be maintained, and so that captured bed bugs may be periodically removed and disposed of.

If desired, the device could also be provided with a carbon dioxide releasing function, a kairomone releasing function, and/or heat so as to attract bed bugs seeking to feed. This could be provided instead of the pheromone release, or in addition to the pheromone release, preferably at a different location within the body of the device, with the possibility of switching between modes, i.e. between attracting bed bugs seeking a harboring location, and bed bugs seeking a feeding location. The switching could be based on time of day, for example, using the clock function of the device. Heat, if employed, could be generated inherently by the operation of the device, or a small heating element could be provided.

Desk Lamp

Figure 9:
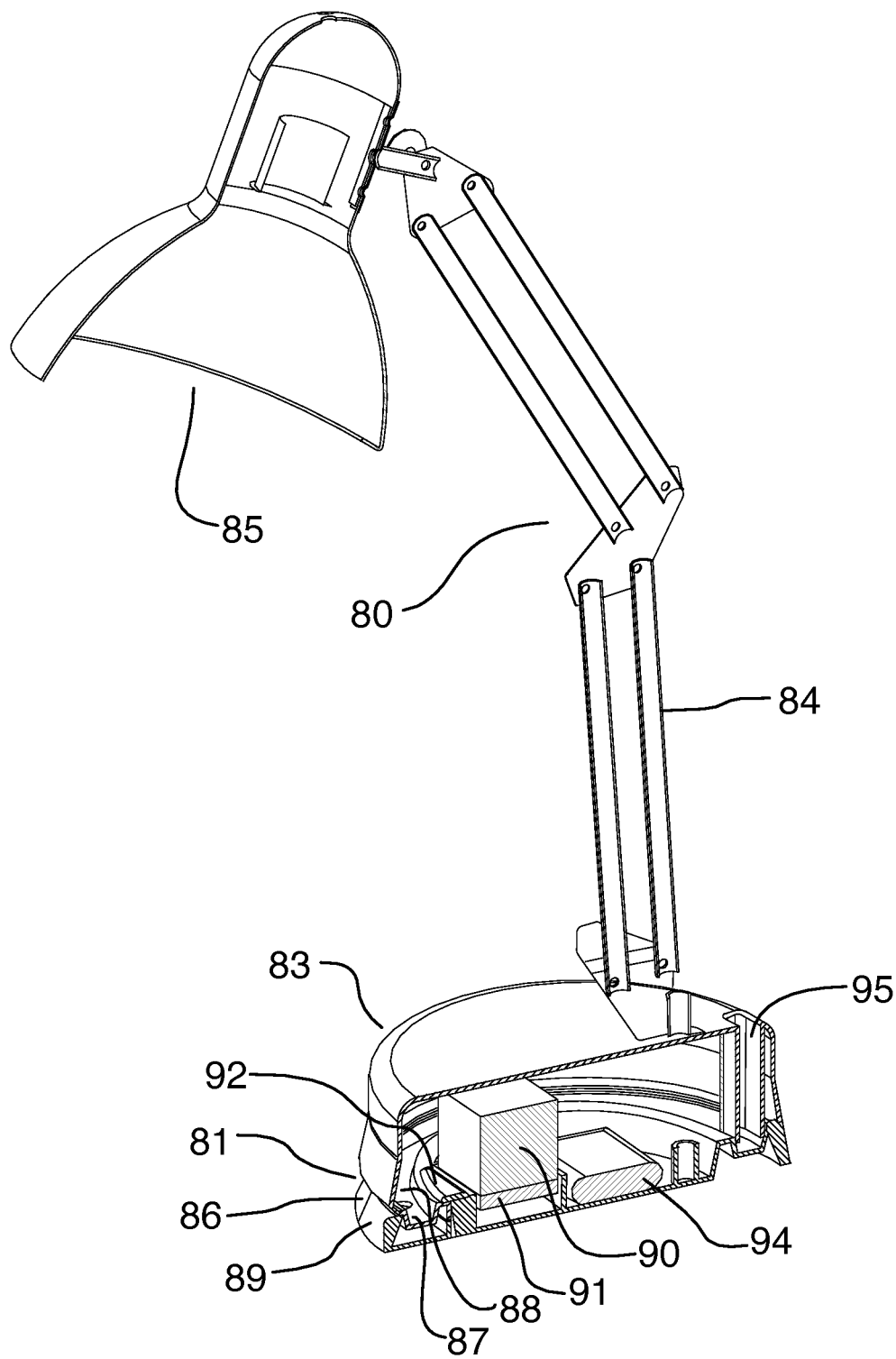
FIG. 9 is a cutaway perspective view of a desk lamp incorporating a bed bug trap.

FIG. 9 shows an example of a desk lamp 80 according to the invention. The base of the lamp is configured as a pitfall trap, there being a gap 81 between the bottom portion of the base, and an upper portion 83 on which the lamp arm 84 and lamp 85 are mounted. Bed bugs climb the textured outer surface 86 of the bottom portion, and fall into the channel 87. From there, they migrate to a hole 88 and fall through it onto the upper surface of a removable and replaceable drawer 89. As in other embodiments, this upper surface of the drawer carries a glue strip to trap the bed bugs.

Preferably, the base includes a heating element 90 above a kairomone puck 91, the heating element and kairomone serving to attract bed bugs seeking to feed. The kairomone escapes into the pitfall trap via a small port 92. Preferably, the base may also include a pheromone-releasing puck 94, preferably with a pheromone release passageway (not specifically illustrated) leading therefrom towards a high pitfall 95 for attracting bed bugs seeking to harbor. The outside of the lamp base is continuous and textured in the area of the high pitfall so that bed bugs seeking a harboring location can climb. Bed bugs fall from the high pitfall down onto the channel 87 and thence ultimately through the hole 88 and onto the glue strip.

Unpowered Versions

As discussed above, although powering the device is preferable, especially for combining with other functions such as an alarm clock, radio or clock radio, or to aid in switching between modes, the invention is not limited to powered devices. Even in a two-mode device where switching between modes is desired, that may be accomplished manually, or for example by means of a non-electric timer and timing mechanism. Carbon dioxide generation is not power dependent, nor is the release of semiochemicals (pheromones or kairomones). Heat, if desired, may be generated by small heat packs such as those commonly sold in cold countries for hand warming, where exposure to air produces a slow exothermic reaction to generate warmth. Alternatively, the device could be positioned near a plant, such that the plant acts as a carbon dioxide source, and/or near a computer or lamp or other heat-generating device, or near a room heating outlet.

In an unpowered version, for example, the device may be given the appearance of a lamp base, sculpture, or appliance of unknown function, i.e. a container or box where the guest cannot determine what the function is.

Within the device, there may be a bed bug trap of the pitfall type, for example, preferably but not necessarily with a glue strip or the like to capture the bed bugs who fall in. There may also be carbon dioxide generation by any suitable means as described in the above examples or as further described below.

Preferably, the unpowered device also includes the two modes described above, namely the use of a pheromone to attract bed bugs to a harboring area, and the use of a kairomone, preferably with carbon dioxide and/or heat, to attract bed bugs seeking to feed.

Figure 10:
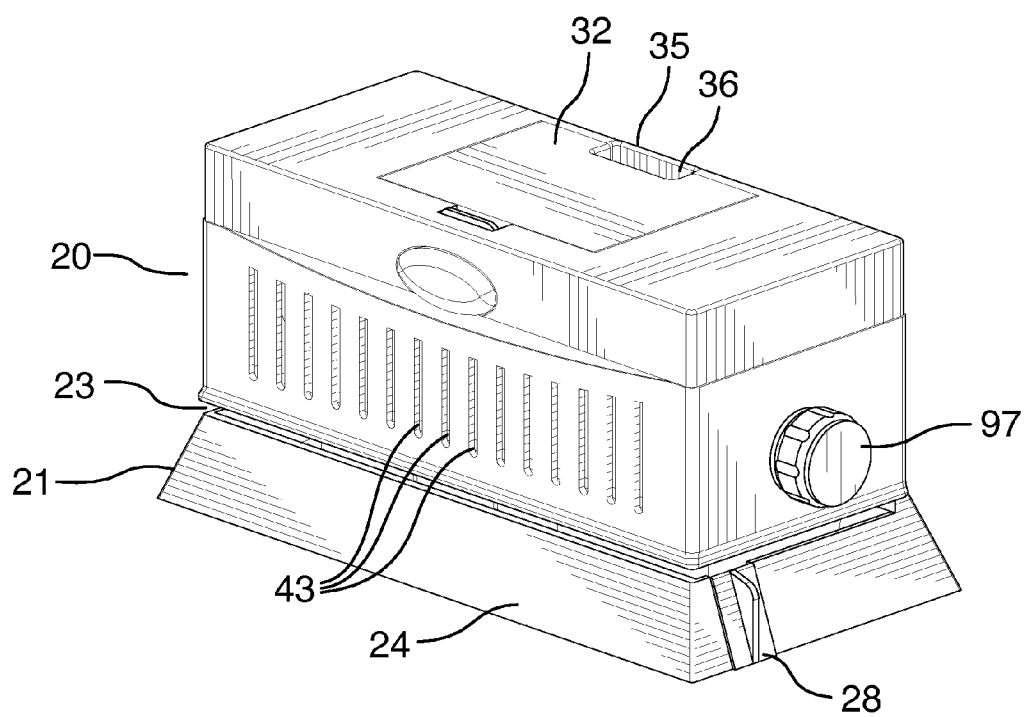
FIG. 10 is a front perspective view of an unpowered version of the device, which may be especially suited to hotel use.
Figure 11:
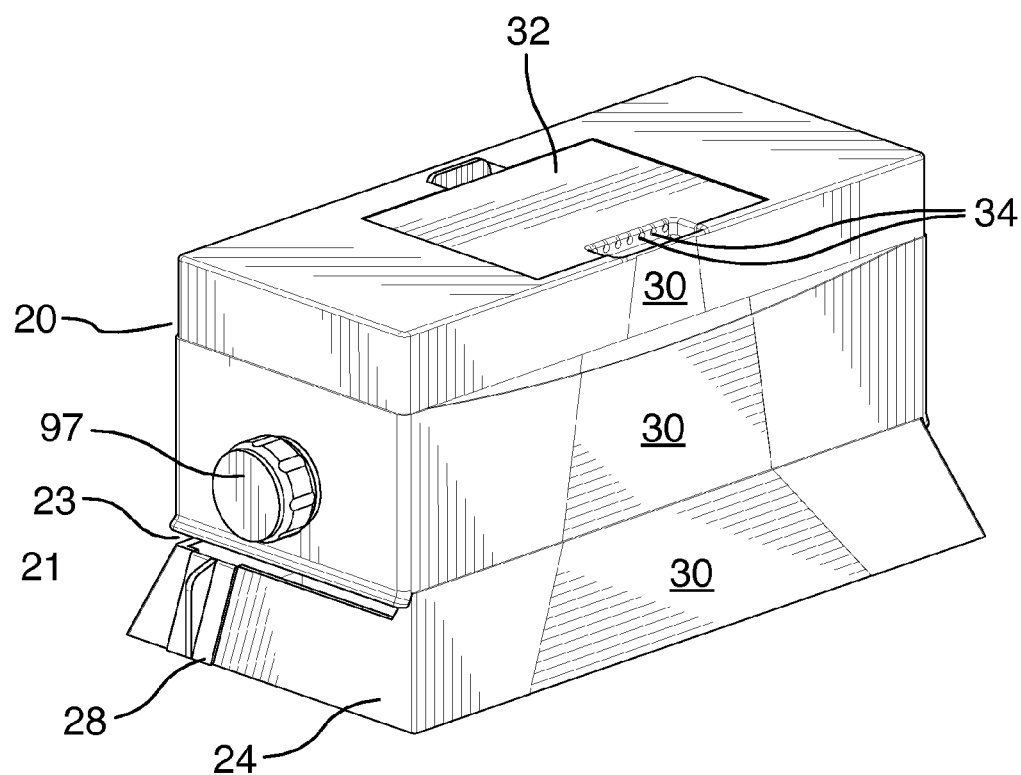
FIG. 11 is a rear perspective view of the FIG. 10 device.
Figure 12:
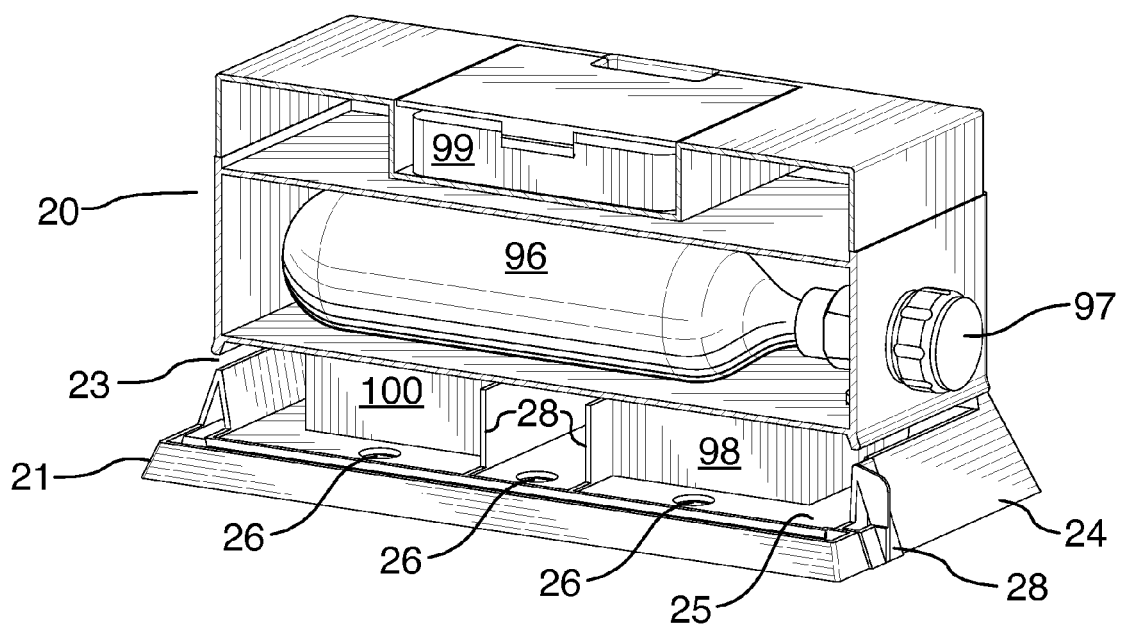
FIG. 12 is a front cutaway perspective view corresponding to FIG. 10.

FIGS. 10-12 show an example of such an unpowered device. The device is intended to sit on the floor of a room, for example a hotel room, perhaps in an unobtrusive location such as under a bed or bedside table or desk. Alternatively, it could be mounted to a wall or to the side of a bed frame or piece of furniture, by a suction cup or cups, by an adhesive (a peel-back strip on the back of the device, for example), or by the use of hook and pile fastening material (e.g. Velcro brand fastening).

The device of FIGS. 10-12 provides two trapping modes, without the use of power. Its basic structure is similar to that of the device of FIGS. 3-7, as can readily be seen from a comparison of the drawings, such that there is no need to repeat the full description. Reference numbers corresponding to those of FIGS. 3-7 are shown in FIGS. 10-12 where appropriate. Where the device differs from the device of FIGS. 3-7 is that carbon dioxide, instead of being generated by tablets and water, is dispensed from a carbon dioxide cartridge 96, the release being controlled by a manual valve 97; and heat, instead of being generated by a heating element, is generated by the aforementioned heat pack 98, or alternatively by a battery-operated heating element in place of the heat pack.

As with the device of FIGS. 3-7, this device includes an upper area with a pheromone puck 99 to attract bed bugs seeking a harboring location, and a lower area with a a kairomone puck 100, pitfall trap, glue strip, etc. as in the device of FIGS. 3-7. A chute 36 from the upper area preferably leads down to the base as in the device of FIGS. 3-7, leading bed bugs ultimately through the holes and onto the glue strip, as in the device of FIGS. 3-7.

Although this device preferably has heat, carbon dioxide and both kairomone and pheromone release, it should be understood that it could still function to attract bed bugs seeking a feeding location with just kairomone, or just kairomone and carbon dioxide, or just heat and carbon dioxide, or just heat and kairomone, depending on the user's needs and desires and cost factors. Alternatively, it could act to mimic a harboring location only, by providing a pheromone without a kairomone, carbon dioxide or heat.

Furthermore, it should be noted that it is not necessary that there be a trapping means for both harboring and feeding locations. Devices such as these may often be used primarily for detection of a bed bug problem, often with no expectation that they will be sufficient to actually rid the room of the problem once detected. When functioning primarily as a detection device, the harboring area in particular may not require trapping means; it will be sufficient to examine the harboring area for the presence of any bed bugs there (alive or dead), or for evidence that they have been there.

Carbon Dioxide Production Methods

Carbon dioxide generation is primarily desirable when trying to attract bed bugs seeking a feeding location. However, most of the time bed bugs are more interested in finding a safe harboring location, rather than a feeding location. In addition, a constant supply of carbon dioxide would require excessively frequent replacement. It is therefore preferable that the carbon dioxide generation and use be intermittent. Even when trying to attract bed bugs seeking a feeding location, it may not be necessary or desirable to generate carbon dioxide continuously. Therefore, some metering means and/or shutoff means is highly desirable, though in some cases it may be acceptable or even desirable to have a continuous slow release, despite the more frequent maintenance which that may entail.

In addition to the carbon dioxide generation means described above, other carbon dioxide generation means could include a compressed carbon dioxide canister with a suitable metering valve; a liquid acid, e.g. acetic acid (vinegar) with a solid carbonate, e.g. sodium bicarbonate (baking soda), in tablet or powder form; a solid acid, such as anhydrous citric acid with a solid carbonate, e.g. sodium bicarbonate (baking soda) and water; via fermentation (e.g. yeast and sugar); or any other known method of producing and/or dispensing carbon dioxide.

Semiochemical Release Mechanisms

The semiochemicals (pheromones and/or kairomones) can be released by a variety of methods, including the following, for example:

a. A porous surface, such as felt, sponge, cork or the like, saturated with the pheromone or kairomone, such that the pheromone or kairomone is released as it evaporates.

b. An impregnated gel (such that the pheromone or kairomone is combined with the gel material, and is released as it dries)

c. The pheromone or kairomone can be impregnated into an adhesive, exposed by removing release paper (like magazine fragrance samples)

d. In a configuration like a mothball (where it reacts with moisture in the air and eventually dissolves)

e. In a selectively permeable material, where the pheromones or kairomones are in a container with a selectively permeable membrane lid, where the membrane allows evaporated gas to pass through but not liquid.

f. In a "puck" or the like, in combination with air freshening compositions or other substances.

In the case of the bed bug trap combined with an air freshener, the pheromones or kairomones may conceivably be combined with the air freshening composition. Thus when attempting to attract bed bugs to a harboring location, for example, pheromones may be released along with air freshening compositions. If the device is a two-mode device as described above, and the mode to attract bed bugs for feeding is activated, it may be that the pheromone generation is continued, or that it is stopped along with the release of the air freshening composition. Or, the air freshening compositions may be released only when the "feeding mode" is activated, i.e. along with kairomones, heat and/or carbon dioxide generation. Or the air freshening compositions may be released in both modes, including when operating simultaneously. The heating element may be used to help produce the release of the kairomones and of the air freshening composition.

The air freshening composition is not part of this invention. Any conventional air freshening composition may be used, in any convenient form, the replaceable "puck" form being particularly useful, especially to the extent that it may facilitate incorporating the desired semiochemicals. One puck may combine a suitable pheromone with an air freshening composition, and another may combine a suitable kairomone with an air freshening composition.

Additional Variations

It will be evident to those knowledgeable in the field of the invention that many variations on the examples described above are conceivable within the scope of the invention. It should therefore be understood that the claims which define the invention are not restricted to the specific examples(s) described above.

For example, in some embodiments, a fan may be provided to aid in the dispensing the semiochemical(s) and/or air freshening composition. The fan may also generates warmth to aid in attracting bed bugs.

As discussed above, various other appliances may be combined with the bed bug trap in a complementary fashion, so as to provide the same synergistic results with shared use of certain features, such as a power supply for example. Another example, in addition to those described above, is to incorporate a bed bug trap into a power bar, by providing a compartment for a semiochemical puck, and a harboring and/or feeding mode location or locations. The power bar will normally generate sufficient warmth to act as an attractant, and the on/off switch of the power bar may be used as a trigger for activating the feeding mode.

Finally, it should be appreciated that the various traps described above could conceivably be adapted to trapping other insects which are responsive to heat, carbon dioxide and/or semiochemicals, with such selections of semiochemicals as may be appropriate for the particular insects. The selection of which attractants to use may of course vary depending on the insect being targeted, as may the specific configuration of the trapping elements.

Further variations may be apparent or become apparent to those knowledgeable in the field of the invention, within the scope of the invention as defined by the claims which follow.

The invention claimed is:

1. A bed bug trap, having bed bug attracting means and bed bug trapping means within a housing, wherein said bed bug attracting means comprises at least two of the group consisting of: carbon dioxide, from carbon dioxide generating or dispensing means; heat, generated by a heat source; and at least one semiochemical, from semiochemical emitting means;

wherein said bed bug attracting means has two bed bug attraction modes, namely a first mode providing a first said semiochemical for attracting bed bugs seeking a harboring location to a first area of said trap, and a second mode providing a second said semiochemical for attracting bed bugs seeking a feeding location to a second area of said trap; and wherein at least one of said heat and said carbon dioxide are provided at said second area of said trap and not at said first area of said trap.

2. A bed bug trap as in claim 1, wherein said housing also provides the function of a complementary appliance, wherein the appliance is powered by a power supply, and wherein the power supply is used for releasing heat to attract bed bugs or to release the semiochemical.

3. A bed bug trap as in claim 1, wherein said first semiochemical is a pheromone and wherein said second semiochemical is a kairomone.

4. A bed bug trap as in claim 1, wherein at least one pitfall trap is positioned such that bed bugs arriving into at least one of said first and second areas can fall into said pitfall trap.

5. A bed bug trap as in claim 4, wherein there is a single pitfall trap positioned such that bed bugs arriving into either one of said first and second areas can fall into said pitfall trap.

6. A bed bug trap as in claim 2, wherein said complementary appliance is an air freshener adapted to dispense an air freshening composition.

7. A bed bug trap as in claim 6, wherein said dispensing of an air freshening composition being combined with release of at least one semiochemical for attracting bed bugs.

8. A bed bug trap as in claim 7, wherein said air freshening composition and at least one semiochemical are embodied in a puck which gradually releases said air freshening composition and said at least one semiochemical.

9. A bed bug trap as in claim 8, where said semiochemical is a pheromone to attract bed bugs seeking a harboring location.

10. A bed bug trap as in claim 8, where said semiochemical is a kairomone, said bed bug trap being further characterized by a heating element used to provide heat as a bed bug attractant, and to warm said an air freshening composition to stimulate or enhance its release.

11. A bed bug trap as in claim 1, further comprising a removable element which includes a glue strip for capturing bed bugs, whereby bed bugs may be removed from the trap by removing the removable element.

12. A bed bug trap as in claim 4, further comprising a removable element which includes a glue strip for capturing bed bugs, whereby bed bugs may be removed from the trap by removing the removable element.

* * * * *